(12) United States Patent
Hwang et al.

(10) Patent No.: US 8,252,950 B2
(45) Date of Patent: Aug. 28, 2012

(54) POROUS ORGANIC-INORGANIC HYBRID MATERIALS WITH CRYSTALLINITY AND METHOD FOR PREPARING THEREOF

(75) Inventors: Young Kyu Hwang, Daejeon (KR); Jong-San Chang, Daejeon (KR); You-Kyong Seo, Busan (KR); Dong Won Hwang, Gyeonggi-do (KR)

(73) Assignee: Kora Research Institute of Chemical Technology (KR)

( * ) Notice: Subject to any disclaimer, the term of this patent is extended or adjusted under 35 U.S.C. 154(b) by 294 days.

(21) Appl. No.: 12/629,843

(22) Filed: Dec. 2, 2009

(65) Prior Publication Data

US 2011/0118490 A1    May 19, 2011

(30) Foreign Application Priority Data

Nov. 19, 2009  (KR) .................. 10-2009-0111938

(51) Int. Cl.
- *C07F 15/02* (2006.01)
- *C07F 5/06* (2006.01)
- *C07F 11/00* (2006.01)
- *C07F 9/00* (2006.01)

(52) U.S. Cl. ........... 556/44; 556/138; 556/147; 428/116

(58) Field of Classification Search .................. 556/138, 556/147, 44; 428/116
See application file for complete search history.

(56) References Cited

U.S. PATENT DOCUMENTS

| | | | |
|---|---|---|---|
| 6,675,601 B2 | 1/2004 | Ebara | 62/271 |
| 6,959,875 B2 | 11/2005 | Yabu et al. | 236/44 C |
| 6,978,635 B2 | 12/2005 | Yabu et al. | 62/271 |
| 2010/0160661 A1 | 6/2010 | Schubert et al. | |

FOREIGN PATENT DOCUMENTS

| | | |
|---|---|---|
| KR | 0803945 B1 | 2/2008 |
| KR | 2008-0091225 A | 10/2008 |
| KR | 20080114380 A | 12/2008 |
| WO | WO 2007/105871 A1 | 9/2007 |
| WO | WO 2008/066293 A1 | 6/2008 |
| WO | WO 2008/072896 A1 | 6/2008 |

OTHER PUBLICATIONS

Susumu Kitagawa et al., "Functional Porous Coordination Polymers", *Angew. Chem. Intl. Ed.*; 2004, 43, 2334-2375.

Stuart L. James, "Metal-organic frameworks", *Chem. Soc. Rev.*, 2003, 32, 276-288.

G. Férey et al., "A Chromium Terephthalate-Based Solid with Unusually Large Pore Volumes and Surface Area", *Science*, 2005, 309, 2040-2042.

Patricia Horcajada et al., "Synthesis and catalytic properties of MIL-100(Fe), an iron(III) carboxylate with large pores", *Chemical Communication*, 2007, 2820-2822.

G. Férey et al., "Crystallized Frameworks with Giant Pores: Are There Limits to the Possible?" *Accounts of Chemical Research*, 2005, 38, 217-225.

M.J. Rosseinsky, "Recent developments in metal-organic framework chemistry: design, discovery, permanent porosity and flexibility", *Microporous Mesoporous Materials*, 2004, 73, 15-30.

*Primary Examiner* — Porfirio Nazario Gonzalez
(74) *Attorney, Agent, or Firm* — Martine Penilla Group, LLP

(57) ABSTRACT

Porous organic-inorganic hybrid materials with crystallinity and a method for preparing the same are provided. The method comprises preparing a reaction solution containing a mixture of at least one inorganic metal precursor, at least one organic compound which may act as a ligand, and a solvent (step 1); and forming porous organic-inorganic hybrid materials with crystallinity by reacting the reaction solution (step 2), wherein the reaction is carried out under the pressure of about 3 atm or less.

7 Claims, 1 Drawing Sheet

POROUS ORGANIC-INORGANIC HYBRID MATERIALS WITH CRYSTALLINITY AND METHOD FOR PREPARING THEREOF

CROSS-REFERENCE TO RELATED APPLICATIONS

This patent application claims priority from and is related to Korean Patent Application No. 2009-0111938 filed Nov. 19, 2009, entitled "Porous Organic-Inorganic Hybrid Materials With Crystallinity And Method For Preparing Thereof." Korean Patent Application No. 2009-0111938 is incorporated by reference in its entirety herein.

TECHNICAL FIELD

Porous organic-inorganic hybrid materials with crystallinity and a method for preparing the same are provided.

BACKGROUND

In general, the term "porous organic-inorganic hybrid materials" is also referred to as "porous coordination polymers" [Angew. Chem. Intl. Ed., 43, 2334 (2004)] or "metal-organic frameworks" [Chem. Soc. Rev., 32, 276 (2003)].

The porous organic-inorganic hybrid materials have been recently further developed through the integration of molecular engineering and material science. Said material(s) has a large surface area and pores of molecular size or nano size, and thus can be used not only for adsorbents, gas storage materials, sensors, membranes, functional thin films, drug delivery materials, catalysts, catalyst carriers, etc., but also for encapsulating guest molecules smaller than their pore size or separating molecules according to the sizes of the molecules by using their pores. Thus, said material(s) has recently been actively studied.

Particularly, porous organic-inorganic hybrid materials with crystallinity can be defined as porous organic-inorganic polymer compound(s) having a central metal ion bonded to an organic ligand. The term porous organic-inorganic hybrid materials with crystallinity also refer to a crystalline compound with pores of a molecular size or nano size, including both organic material and inorganic material in its framework structure.

Porous organic-inorganic hybrid materials have usually been prepared by a solvothermal synthesis, but a hydrothermal synthesis including adding acid in order to increase the hydrothermal stability has also been used. As representative porous organic-inorganic hybrid materials prepared by the hydrothermal synthesis, $Cr_3O(H_2O)_2F[C_6H_3—(CO_2)_3]_2 \cdot nH_2O$ (n~14.5), $Fe_3O(H_2O)_2F[C_6H_3—(CO_2)_3]_2 \cdot nH_2O$ (n~14.5), and $Cr_3F(H_2O)_2O[C_6H_4(CO_2)_2]_3 \cdot nH_2O$ (n~25) have been reported [Science 23, 2040, 2005; Chemical Communication 2820, 2007, Accounts of Chemical Research, 38, 217, 2005]. However, in the case of using hydrofluoric acid as a crystallization agent under high pressure as in the prior methods, in the selection of a reactor for scale-up process on preparing porous organic-inorganic hybrid materials, there is a severe limitation in selecting a reactor other than the Teflon reactor. In addition, the prior methods involve relatively high waste treatment costs. Recently, Korean Patent Application No. 2007-0063881 has disclosed a method for preparing porous organic-inorganic hybrid materials using a reaction solution including nitric acid, but not using hydrofluoric acid as a crystallization agent in prior methods for preparing porous organic-inorganic hybrid materials. However, methods for preparing porous organic-inorganic hybrid materials have to be carried out under high pressure of 3 atm or more. Particularly, the methods have to be carried out using a high concentration (5% or higher) of acid at high pressure (3 atm or more) and high temperature, and thus there has been a severe limitation in selecting a reactor.

Meanwhile, an adsorbent that can easily adsorb and desorb water has various uses. For example, a dehumidifier may utilize the adsorbent having a property of adsorbing water at low temperature and desorbing water when it is heated to high temperature. In addition, in case where an adsorbent is used in coolers/heaters, during heating operation, the adsorbent can act as a humidifier by adsorbing the outdoor moisture of low temperature, introducing the moisture to the indoor, and desorbing it in the indoor where the temperature is high; and during cooling operation, the adsorbent can achieve a comfortable indoor atmosphere by adsorbing the indoor moisture of low temperature, taking it to the outside and desorbing it in the outdoor where the temperature is high. Air-conditioners and humidity controllers applying such ideas have been suggested in U.S. Pat. Nos. 6,978,635, 6,959,875, 6,675,601, etc. However, the patents do not describe the adsorbent used in such devices in detail, but only mention that silica gel, zeolite, ion exchange resin are used, or that an adsorbent is used. In addition, such adsorbents not only have a low adsorption amount, but also cause the operation costs to rise by requiring a high temperature of at least 100° C. for desorption, etc.

Recently, Korean Patent No. 806586 has reported the case of using porous organic-inorganic hybrid materials capable of adsorbing and desorbing water even at low temperature. However, according to the patent, porous organic-inorganic hybrid materials have to be crystallized such that they have a surface area of at least 1,000 $m^2/g$ and a pore volume of at least 1.0 ml/g. Accordingly, the technology requires an additional purification process, which leads to very high manufacturing costs.

Therefore, it is necessary to develop an adsorbent that can desorb even at low temperature and has a large difference between the adsorption amount and the desorption amount by an economical process. However, there have always been problems that in case the adsorption amount is high, desorption is difficult, and in case the adsorption amount is low, the difference between the adsorption amount and the desorption amount is small.

In addition, until now, Activated carbon and hydrophobic zeolite have been mainly used as adsorbents that can remove organic compounds present in an indoor space. Activated carbon has a very large surface area due to a number of nano pores, and has a strong adsorption strength to non-polar molecules, and thus has an excellent effect in removing exhaust gas, removing smell and odor, whereas zeolite is a hydrophilic adsorbent having a pore diameter of about 3-10 Å and thus has a strong adsorption property to carbon monoxide, carbon dioxide and water. However, most adsorbents only have hydrophobic or hydrophilic properties, and thus have disadvantages that they cannot effectively adsorb and remove volatile organic compounds including water.

Accordingly, the present inventors developed porous organic-inorganic hybrid materials with crystallinity having uniform particle sizes, obtained under the synthesis conditions of a low pressure of 3 atm or less and high concentration (the molar ratio of solvent to metal precursor is 100 or less). The present inventors confirmed that an adsorbent including said porous organic-inorganic hybrid materials with crystallinity can easily adsorb and desorb water even at low temperature, and thus can be used as a water adsorbent, heat pump, desiccant, adsorbent/desiccant for sewage treatment, adsorbent for a refrigerating machine, and adsorbent for an air conditioner or cooler, and the present inventors also confirmed that an adsorbent including said porous organic-inorganic hybrid materials with crystallinity has excellent adsorption properties to volatile organic compounds (VOCs) as compared with conventional adsorbents. Thereby, the present inventors achieved the present invention.

SUMMARY

Porous organic-inorganic hybrid materials with crystallinity and a method for preparing the same are provided. In one embodiment, the method includes preparing a reaction solution including a mixture of at least one inorganic metal precursor, at least one organic compound which may act as a ligand, and a solvent (step 1); and forming porous organic-inorganic hybrid materials with crystallinity by reacting the reaction solution (step 2), where the reaction is carried out under the pressure of about 3 atm or less.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
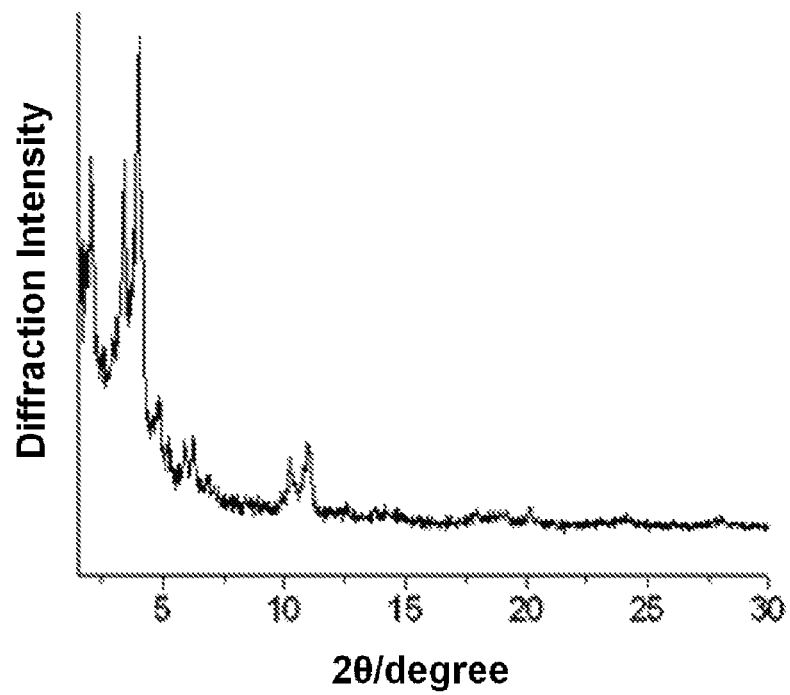
FIG. 1 is an X-ray diffraction pattern result of porous organic-inorganic hybrid materials with crystallinity obtained according to one illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the components of the present disclosure, as generally described herein, and illustrated in the Figures, may be arranged, substituted, combined, and designed in a wide variety of different configurations, all of which are explicitly contemplated and make part of this disclosure.

In one embodiment of the present disclosure, a method is provided for efficiently preparing porous organic-inorganic hybrid materials with crystallinity at a low pressure of 3 atm or less regardless of the presence or absence of hydrofluoric acid, a crystallization agent, and porous organic-inorganic hybrid materials with crystallinity are prepared by the method. The adsorbent including said porous organic-inorganic hybrid materials have excellent adsorption properties to specific materials even at low temperature treatment, and thus can be used as a water adsorbent, heat pump, desiccant, adsorbent/desiccant for sewage treatment, adsorbent for a refrigerating machine, adsorbent for an air conditioner or cooler, catalyst, etc., and can be useful in removing volatile organic compounds (VOCs).

In order to achieve the above objectives, one embodiment of the present disclosure provides a method for preparing porous organic-inorganic hybrid materials with crystallinity regardless of the presence or absence of hydrofluoric acid, which is a crystallization agent, by remarkably increasing the crystallizing rate under the synthesis conditions of high concentration and establishing a low pressure condition of 3 atm or less by adjusting the automatic adsorption rate of the solvent used.

Despite the low-pressure condition of 3 atm or lower, the present disclosure can provide porous organic-inorganic hybrid materials with crystallinity having high crystallinity and uniform particle sizes by remarkably increasing crystallizing rate under the synthesis conditions of high concentration and adjusting the crystal growth rate and the automatic adsorption rate of solvent during reaction in the preparation of the porous organic-inorganic hybrid materials with crystallinity.

Particularly, in case where the porous organic-inorganic hybrid materials according to one embodiment of the present disclosure are used as a water adsorbent, the adsorbent can easily desorb water at a low temperature of 100° C. or lower. Since the adsorbent easily adsorb and desorb water at low temperature and have excellent adsorption/desorption properties to gas phase compounds and liquid phase compounds, the adsorbent can be used as a water adsorbent, heat pump, desiccant, adsorbent/desiccant for sewage treatment, adsorbent for a refrigerating machine, adsorbent for an air conditioner or cooler and catalyst. In addition, in the case of using the porous organic-inorganic hybrid materials with crystallinity as a catalyst or adsorbent for removing indoor pollutants present in an indoor space, it is possible to effectively remove specific hazardous materials. Thus, the porous organic-inorganic hybrid materials with crystallinity can be useful in preventing sick house syndrome and removing a variety of hazardous materials.

In one embodiment, porous organic-inorganic hybrid materials with crystallinity are prepared by a method including:
preparing a reaction solution including a mixture of at least one inorganic metal
precursor, at least one organic compound which may act as a ligand, and a solvent (step 1); and
forming porous organic-inorganic hybrid materials with crystallinity by reacting the reaction solution (step 2),
where the reaction is carried out under the pressure of about 3 atm or less.

Hereinafter, we will describe each of the steps of the method for preparing porous organic-inorganic hybrid materials with crystallinity in detail.

In one embodiment of the method for preparing porous organic-inorganic hybrid materials with crystallinity, step 1 is a process for preparing a reaction solution including a mixture of at least one inorganic metal precursor, at least one organic compound which may act as a ligand, and a solvent.

Examples of the compound including a metal that can be used as an inorganic metal precursor include at least one metal halide or a hydrate thereof, metal nitrate or a hydrate thereof, metal sulfate or a hydrate thereof, metal acetate or a hydrate thereof, metal salt such as metal carbonyl and metal alkoxide, or a hydrate thereof. In one embodiment, any metal can be used as a metal component included in the porous organic-inorganic hybrid materials with crystallinity. The transition metal components include Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Mg, Ca, Sr, Ba, Sc, Y, Al, Ga, In, Tl, Si, Ge, Sn, Pb, As, Sb, Bi, etc. In particular, transition metals which easily form a coordination compound are suitable. In some embodiments, among transition metals, chromium, vanadium, iron, nickel, cobalt, copper, titanium, zirconium, manganese, etc. are preferable, and chromium and iron are quite preferable. In another embodiment, in addition to transition metals, typical elements forming a coordination compound and metals such as lanthanide can also be used. Among elements, aluminum and silicon are suitable, and among lanthanide metals, cerium, yttrium, terbium, europium, and lanthanum are suitable. As a metal source, not only metal itself but also any compound of metal can be used.

As an organic compound which may act as a ligand which is another component of porous organic-inorganic hybrid materials with crystallinity, referred to as a linker, any organic compound having a functional group which can form coordinate bonds can be used. In some embodiments, examples of functional groups which can form coordinate bonds include, but are not limited to, carboxyl group, anion group of carboxylic acid, amino group (—NH$_2$), imino group

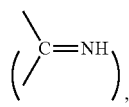

Amide group (—CONH$_2$), sulfonic acid group (—SO$_3$H), anion group of sulfonic acid (—SO$_3^-$), methanedithioic acid group (—CS$_2$H), anion group of methanedithioic acid (—CS$_2^-$), pyridine group, pyrazine group, etc.

In one embodiment, examples of organic ligands include organic compounds having at least two sites for coordination, e.g., polydentate organic compounds such as bidentate organic compounds and tridentate organic compounds. Examples of said organic ligands include neutral organic compounds such as bipyridine, pyrazine, etc., anionic organic compounds, e.g., anions of carboxylic acid such as terephthalate, naphthalenedicarboxylate, benzenetricarboxylate, benzentribenzoate, pyridinedicarboxylate, bipyridyldicarboxylate, etc., having a site for coordination. In one embodiment, as the carboxylate derivative, carboxylate having Cl, Br, I, NO$_3$, NH$_2$, COOH, SO$_3$H, etc. in its benzene ring is included can be used.

In another embodiment, as the anionic organic ligand of carboxylic acid, in addition to anions having an aromatic ring such as terephthalate, for example, anions of linear carboxylic acid such as formate, oxalate, malonate, succinate, glutamate, hexanedioate, heptanedioate, and anions having a non-aromatic ring such as cyclohexyldicarboxylate can be used, but it is not limited thereto.

In another embodiment, the organic ligand may be dihydroxyterephthalate or a derivative thereof. In some embodiments, as the organic ligand, 2,5-dihydroxyterephthalate or a derivative thereof can be used. In one embodiment, as the dihydroxyterephthalate derivative, dihydroxyterephthalate having Cl, Br, I, NO$_3$, NH$_2$, COOH, SO$_3$H, etc. in its benzene ring can be used.

In another embodiment, as the organic compound which may act as an organic ligand, in addition to an organic compound having a site for coordination, an organic compound which has a potential site for coordination and thus can be converted into a form capable of forming a coordinate bond under reaction conditions can also be used. For example, in case of using an organic acid such as terephthalic acid, terephthalic acid converts into terephthalate after reaction and thus can bond to a metal component. In some embodiments, examples of the organic compounds include organic acids such as benzenedicarboxylic acid, naphthalenedicarboxylic acid, benzenetricarboxylic acid, naphthalenetricarboxylic acid, benzenetribenzoic acid, pyridinedicarboxylic acid, bipyridyldicarboxylic acid, formic acid, oxalic acid, malonic acid, succinic acid, glutamic acid, hexanedioic acid, heptanedioic acid and cyclohexyldicarboxylic acid; and an anion thereof; pyrazine, bipyridine, dihydroxyterephthalic acid, etc. In some embodiments, one or more organic compounds can be used in combination.

In one embodiment, in the step 1, a solvent capable of dissolving both a metal component and organic compound is necessary. As said solvent, any substance, such as water; alcohols such as methanol, ethanol, propanol, etc.; alkylene polyols such as EG (ethylene glycol), glycerol, etc.; polyalkylene polyol such as polyethylene glycol, etc.; ketones such as acetone, methylethyl ketone; hydrocarbons such as hexane, heptane, octane, etc.; N,N-dimethylformamide (DMF); and N,N-diethylformamide (DEF), N,N-dimethylacetamide (DMAc), acetonitrile, dioxane, chlorobenzene, pyridine, N-methylpyrrolidone (NMP), sulfolane, tetrahydrofurane (THF), gamma butyrolactone, and alicylic alcohol such as cyclohexanol can be used, and two or more solvents can be used in combination. On one illustrative embodiment, it is preferable to use water or alcohol as a solvent.

In one embodiment, the step 2 is a process of forming porous organic-inorganic hybrid materials with crystallinity by reacting the reaction solution, where the reaction is carried out under the pressure of about 3 atm or less.

In some embodiments, porous organic-inorganic hybrid materials with crystallinity can be prepared by any conventional method for preparing them. Conventional methods for preparing them include a hydrothermal synthesis, solvothermal synthesis, microwave irradiation, sono synthesis, etc. In one embodiment, porous organic-inorganic hybrid materials can be prepared by solvent dissolving at near room temperature or a hydrothermal synthesis at high temperature using water solvent. In another embodiment, porous organic-inorganic hybrid materials with crystallinity can be prepared by a solvothermal synthesis using an organic solvent [Microporous Mesoporous Mater., vol. 73, p. 15 (2004)]. In another embodiment, porous organic-inorganic hybrid materials with crystallinity are in general prepared by a method of using water or an appropriate organic solvent, conducting a reaction at a temperature higher than the boiling point of the solvent or reaction solution and autogenous pressure, and performing crystallization, similarly to the method for preparing inorganic porous materials such as zeolite and mesoporous compounds. In some embodiments, a metal ion or metal compound and an organic ligand are stirred or microwaves are irradiated on them for a certain time in the presence of a solvent, so that the organic compound coordinates with the metal to form a nucleus. Then, crystallization is performed by microwave-irradiation to the reaction solution in which crystallization nuclei are formed.

In one embodiment, porous organic-inorganic hybrid materials with crystallinity can be prepared by reacting a metal precursor with an organic compound which may act as an organic ligand. In some embodiments, porous organic-inorganic hybrid materials with crystallinity can be prepared by a method including heating a reaction mixture including a metal precursor, an organic compound which may act as an organic ligand, and solvent.

The, the heating temperature of the reaction mixture is not substantially limited. In some embodiments, the heating temperature of the reaction mixture may be room temperature or higher. In another embodiment, the heating temperature of the reaction mixture may be 25° C. or higher, and in yet another embodiment, the heating temperature of the reaction mixture may be 50° C. or higher, 60° C. or higher, 80° C. or higher, or 100° C. or higher. In some embodiments, the heating temperature of the reaction mixture may be 250° C. or lower.

In heating the reaction solution, the reactor pressure is not substantially limited. However, it is convenient to carry out synthesis at an autogeneous pressure of the reactants at reaction temperature. However, in some embodiments, in order to remarkably increase the crystallizing rate under the synthesis condition of high concentration and control the crystal growth rate and the automatic adsorption rate of solvent during reaction, it is preferable to carry out synthesis at a low pressure of 3 atm or less. In some embodiments, the reaction may be carried out at 2.5 atm or less, or at 2 atm or less. Without being bound by theory, it is believed that even in case of using a solvent having a boiling point lower than the reaction temperature, the pressure does not increase since the crystal of porous organic-inorganic hybrid material adsorbs the solvent rapidly. In case of carrying out a reaction under the low pressure condition according to one embodiment, especially in a low pH condition, it is possible to use various types of low-priced reactors instead of an expensive high pressure reactor, which could reduce the investment costs for the preparation of porous organic-inorganic hybrid materials with crystallinity.

In one embodiment, the reaction is carried out under the condition where a metal precursor is present in a reaction solution in a high concentration. For example, the molar ratio of the solvent to the inorganic metal precursor in the reaction solution is 100 or less. In another embodiment, the molar ratio of the solvent to the inorganic metal precursor in the reaction solution is 60 or less, 50 or less, or 25 or less. When the reaction is carried out under high pressure conditions, the crystallizing rate for porous organic-inorganic hybrid materials and/or the yield of the porous organic-inorganic hybrid materials with crystallinity obtained per unit reactor volume can be increased.

The method for preparing porous organic-inorganic hybrid materials with crystallinity according to another embodiment may further include purifying an impurity in the porous organic-inorganic hybrid materials obtained in the step 2 by treatment with an inorganic salt, an acid adjuster, a solvent, or a mixture thereof. This step may be additionally carried out for increasing the surface area of porous organic-inorganic hybrid materials by removing the chelated organic or inorganic impurities from the pores by using a solvent, inorganic salt, acid adjuster or a mixture thereof, in order to remove metal salts and their counter ions or organic ligands present in the pores of porous organic-inorganic hybrid materials with crystallinity.

Examples of the inorganic salt according to one embodiment include a monovalent or divalent cation selected from the group consisting of ammonium ($NH_4^+$), alkali metals and alkaline earth metals, and a monovalent or divalent anion selected from the group consisting of carbonate anion ($CO_3^{2-}$), nitrate ion and sulfate ion. In some embodiments, examples of the inorganic salt include salts having $Ca^{2+}$ or $Mg^{2+}$ as a divalent cation. In another embodiment, examples of the inorganic salt include salts having $F^-$, $I^-$ or $Br^-$ as a monovalent anion. In another embodiment, examples of the inorganic salt include salts having a monovalent cation and divalent anion. In one illustrative embodiment, examples of the inorganic salt include $NH_4F$, KF, KI, or KBr.

The use of an acid adjuster can reduce the time for the purification of porous organic-inorganic hybrid materials with crystallinity, and thus can make the process economical.

In one embodiment, a basic compound can be used as a pH adjuster. In one specific embodiment, ammonia or potassium hydroxide can be used.

As the porous organic-inorganic hybrid materials with crystallinity according to one embodiment, at least one compound selected from the compounds represented by the following formulas or a hydrate thereof are suitable:

(M=Fe, Mn, Cr, V, Al, Ti, Zr or Mg; X=Cl, Br, I, F or OH; Z or Z'=H, $NH_2$, Br, I, $NO_2$ or OH; $0 \leq y \leq 4$);

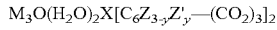

(M=Fe, Mn, Cr, V, Al, Ti, Zr or Mg; X=Cl, Br, I, F or OH; Z or Z'=H, $NH_2$, Br, I, $NO_2$ or OH; $0 \leq y \leq 3$);

($0 \leq y \leq 1$; M=Fe, Mn, Cr, V, Al, Ti, Zr or Mg; X=Cl, Br, I or F); and

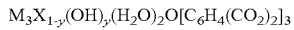

($0 \leq y \leq 1$; M=Fe, Mn, Cr, V, Al, Ti, Zr or Mg; X=Cl, Br, I or F).

In another embodiment, the porous organic-inorganic hybrid materials with crystallinity are at least one compound selected from the compounds represented by the following formulas and a hydrate thereof:

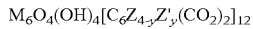

(M=Ti, Sn or Zr; Z or Z'=H, $NH_2$, Br, I, $NO_2$ or OH; $0 \leq y \leq 4$); and

(M=Ni, Co, Mg, Mn or Fe; dhtp=2,5-dihydroxy terephthalic acid).

In one embodiment, the porous organic-inorganic hybrid materials with crystallinity are prepared by a method including:
preparing a reaction solution including a metal precursor, an organic compound which may act as a ligand, and a solvent; and
heating the reaction solution.

In dome embodiments, the porous organic-inorganic hybrid materials with crystallinity may be represented by the formula of

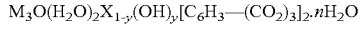

($0 \leq y \leq 1$; M=Cu, Fe, Mn, Cr, V, Al, Ti, Zr or Mg; X=Cl, Br, I or F; $0 \leq n \leq 100$) or the formula of

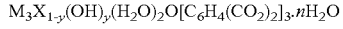

($0 \leq y \leq 1$; M=Cu, Fe, Mn, Cr, V, Al, Ti, Zr or Mg; X=Cl, Br, I or F; $0 \leq n \leq 100$), where X may be partially substituted with —OH.

In one embodiment, examples of the porous organic-inorganic hybrid materials with crystallinity include copper terephthalate, iron terephthalate, manganese terephthalate, chromium terephthalate, vanadium terephthalate, aluminum terephthalate, titanium terephthalate, zirconium terephthalate, magnesium terephthalate, copper benzenetricarboxylate, iron benzenetricarboxylate, manganese benzenetricarboxylate, chromium benzenetricarboxylate, vanadium benzenetricarboxylate, aluminum benzenetricarboxylate, titanium benzenetricarboxylate, zirconium benzenetricarboxylate, magnesium benzenetricarboxylate, a derivative thereof, a solvate thereof, a hydrate thereof or a combination thereof.

In one illustrative embodiment, examples of the porous organic-inorganic hybrid materials with crystallinity include copper terephthalate, iron terephthalate, chromium terephthalate, aluminum terephthalate, copper benzenetricarboxylate, iron benzenetricarboxylate, chromium benzenetricarboxylate, aluminum benzenetricarboxylate, iron naphthalenedicarboxylate, chromium naphthalenedicarboxylate, aluminum naphthalenedicarboxylate, iron benzenetribenzoate, chromium benzenetribenzoate, aluminum benzenetribenzoate, titanium benzenetribenzoate, a derivative thereof, a solvate thereof, a hydrate thereof or a combination thereof. In one embodiment, as the carboxylate derivative, carboxylate having Cl, Br, I, $NO_3$, $NH_2$, COOH, $SO_3H$, etc. in its benzene ring can be used.

In one embodiment, the porous organic-inorganic hybrid materials with crystallinity may include at least two ligands selected from terephthalate, benzenetribenzoate, benzenetricarboxylate and naphthalenedicarboxylate, and a metal element.

In one embodiment, the larger the surface area and/or pore volume of the porous organic-inorganic hybrid materials is, the better the adsorption efficiency is. In some embodiments, the surface area of the porous organic-inorganic hybrid materials may be at least 300 $m^2/g$. In another embodiment, the surface area of the porous organic-inorganic hybrid materials may be at least 500 $m^2/g$, at least 700 $m^2/g$, at least 1,000 $m^2/g$, at least 1,200 $m^2/g$, at least 1,500 $m^2/g$, or at least 1,700 $m^2/g$, but it is not limited thereto. In some embodiments, the surface area of the porous organic-inorganic hybrid materials may be 10,000 $m^2/g$ or less. In one embodiment, the pore volume of the porous organic-inorganic hybrid materials may be 0.1 mL/g or higher, or 0.4 mL/g or higher. In another embodiment, the pore volume of the porous organic-inorganic hybrid materials may be 10 mL/g or lower.

In one embodiment, the porous organic-inorganic hybrid materials have an unsaturated metal site, and a surface-functionalizing compound binds to the unsaturated metal site. In one embodiment, the surface of the porous organic-inorganic hybrid materials may be modified or functionalized by the binding of a surface-functionalizing compound having various functional groups to the unsaturated metal site of the porous organic-inorganic hybrid material. The term unsaturated metal site refers to an accessible coordination site at the metal after removal of water or solvent from the porous organic-inorganic hybrid material. It also refers to a site where a compound having a functional group can form a covalent bond or coordinate bond. Such surface-functionalization can be carried out according to the disclosure of Korean Patent Publication No. 10-0864313, 10-0816538, etc., incorporated herein by reference.

In one embodiment, the porous organic-inorganic hybrid materials may be in a form of powder, thin film, membrane, pellet, ball, foam, slurry, paste, paint, honeycomb, bead, mesh, fiber, corrugated sheet, or rotor, etc., but is not limited to specific forms. The porous organic-inorganic hybrid materials in a form of thin film or membrane may be prepared by, for example, a method of immersing a substrate to a reaction solution and heating the substrate. In another illustrative embodiment, extrusion-molded article of porous organic-inorganic hybrid materials may be prepared by heating the reaction solution including a mixture of a metal precursor, an organic compound which may act as an organic ligand, and a solvent, and extrusion-molding the thus-prepared porous organic-inorganic hybrid materials in a form of a slurry. In another embodiment, molded article of porous organic-inorganic hybrid materials in a form of a pellet, bead, honeycomb, mesh, membrane, etc. may be prepared using an appropriate organic or inorganic binder.

In some embodiments, the amount of the added organic or inorganic binder is 50% by weight or less based on the total weight of the porous organic-inorganic hybrid materials and powder. In one illustrative embodiment, examples of inorganic binders include, but are not limited to, silica, alumina, boehmite, zeolite, mesoporous material, carbon, graphite, layer-structured compound, metal alkoxide, metal halide, etc., and in another illustrative embodiment, examples of organic binders include, but are not limited to, at least one of alcohol, cellulose, polyvinyl alcohol, polyacrylate, etc.

In some embodiments, examples of the substrate include, but are not limited to, a substrate made of silica, alumina, silicone, aluminum, polypropylene, polyimide, conductive polymer, glass, indium tin oxide (ITO), indium zinc oxide and/or heat resistant polymers, or the above substrate whose surface is modified. In some embodiments, in case the porous organic-inorganic hybrid materials are a nano-sized powder, it has a large surface area and thus exhibits excellent adsorption efficiency when it is used as an adsorbent.

In addition, the present disclosure provides a water adsorbent including the porous organic-inorganic hybrid materials with crystallinity.

The water adsorbent according to one embodiment includes porous organic-inorganic hybrid materials having a relatively uniform crystal shape, and a high surface area, and thus can adsorb 0.1~3 g or 0.1~1 g of adsorbate per 1 g of the adsorbent. The water adsorbent can easily adsorb or desorb adsorbates at 150° C. or lower, preferably at 30~100° C. Further, the present inventors confirmed that the water adsorbent of the present disclosure has excellent humidifying and dehumidifying effects by confirming that it has an initial water adsorption rate more than 1.5 times as high as that of prior porous hybrid materials prepared by using hydrofluoric acid, and has a water adsorption amount more than 3 times as high as that of the prior porous hybrid materials.

In one embodiment, in case of using the porous organic-inorganic hybrid materials with crystallinity as an adsorbent for removing volatile organic compounds (VOCs), etc., they can effectively remove specific hazardous materials; thus, the porous organic-inorganic hybrid materials with crystallinity can be useful in preventing sick house syndrome and removing various hazardous materials. The adsorbent including the porous organic-inorganic hybrid materials with crystallinity can remove volatile organic compounds (VOCs) in gas phase or particulate phase. In one illustrative embodiment, the porous organic-inorganic hybrid materials with crystallinity can effectively remove gas phase or particulate phase materials causing sick house syndrome, such as formaldehyde, acetaldehyde, tar, nitrosoamines and polycyclicaromatic hydrocarbons in addition to volatile organic compounds such as toluene benzene, methylethylketone, etc. By virtue of the above characteristic, the adsorbent including the porous organic-inorganic hybrid materials with crystallinity can be used as a filter for cleaning air.

The porous organic-inorganic hybrid materials with crystallinity according to one embodiment can be used as a heterogeneous catalyst. For example, they can be used as an oxidation catalyst or acid catalyst. In some embodiments, the porous organic-inorganic hybrid materials with crystallinity have activity as an oxidation catalyst in oxidation reactions such as sulfoxidation, epoxidation, phosphine oxidation, Fridel-Crafts benzylation, etc. In another embodiment, the porous organic-inorganic hybrid materials with crystallinity have activity as an acid catalyst in acid catalystic reactions such as alkylation, esterfication, Beckman rearrangement, etc.

In one embodiment, the porous organic-inorganic hybrid materials with crystallinity can be used as applications for adsorption and desorption of gas phase or liquid phase compounds, a water adsorbent, heat pump, desiccant, adsorbent/desiccant for sewage treatment and a sewage treatment apparatus including the same, adsorbent for a refrigerating machine, and adsorption-type air conditioning system. Particularly, in case of being using the porous organic-inorganic hybrid materials with crystallinity as a water adsorbent, they can easily adsorb and desorb water at a low temperature of 100° C. or lower; thus, the porous organic-inorganic hybrid materials with crystallinity can be useful as a humidifying agent or a dehumidifying agent.

Examples described below are to further explain features and advantages of the subject matter of the present disclosure, but not limited to the examples presented below. The subject matter of the present disclosure should not be limited to the specific embodiments and examples described herein. In light of the present disclosure, a skilled artisan may easily perceive that it is possible to modify, substitute, add and combine a part of the constitutions disclosed in the present disclosure other than various illustrative embodiments and examples.

EXAMPLES

Example 1

After adding iron nitrate ($Fe(NO_3)_3 \cdot 6H_2O$) 67 mmol and 1,3,5-benzenetricarboxylic acid (BTCA) 44 mmol to a glass reactor, distilled water was added. The final molar ratio of the reaction material was $Fe(NO_3)_3 \cdot 6H_2O$:BTCA:$H_2O$=1:0.66:11.3. The mixed reaction material was stirred in 500 rpm for 20 minutes at room temperature to make the reaction material uniform. While maintaining the glass reactor including said pre-treated reaction material at 120° C. for 8 hours, crystallization was performed. Then, the reaction material was cooled to room temperature, washed with distilled water and dried to obtain porous organic-inorganic hybrid materials (iron benzenetricarboxylate; Fe-BTC). As a result of measuring the reaction pressure when preparing the porous organic-inorganic hybrid materials (Fe-BTC), the internal pressure at 120° C. was 1 bar. Without being bound by theory, it appears that such low-pressure synthesis process results from that Fe-BTC crystal foamed rapidly adsorbs a solvent at the reaction temperature.

Figure 2:
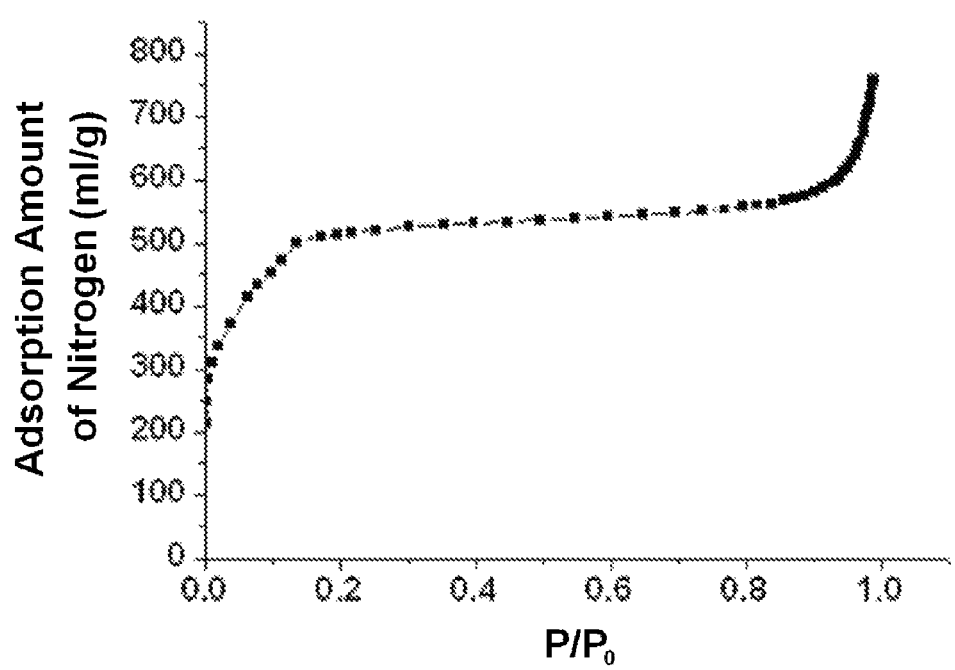
FIG. 2 is a result of a nitrogen adsorption-desorption experiment according to one illustrative embodiment.

It has been confirmed with electron microscope that the prepared porous organic-inorganic hybrid materials were formed with very uniform particle size as nanoparticles of ~200 nm by adjusting nucleate growth rate. It has been confirmed that the X-ray diffraction pattern is same as that of Fe-BTC of a reference [Chemical Communication 2820, 2007] (FIG. 1), but as a result of ICP and EA analysis, it has been confirmed that the obtained porous organic-inorganic hybrid materials Fe-BTC were a material that can be represented by a formula $Fe_3O(H_2O)_2OH[C_6H_3—(CO_2)_3]_2 \cdot nH_2O$ ($0 \leq n \leq 50$) where fluorine was not included. As a result of a nitrogen adsorption-desorption experiment, it has been confirmed that it had a surface area of 1,850 $m^2/g$ and an adsorption amount of 540 mL/g at $P/P_0$=0.5 (FIG. 2). In particular, the yield of the porous organic-inorganic hybrid materials was 150 g per 1 L of reactor. As a result of the analysis of electron microscope, it can be shown that the particle size became very small to 50~500 nm and below.

Porous organic-inorganic hybrid materials with improved surface area was prepared by removing impurities within the pores of hybrid materials after adding the prepared porous organic-inorganic hybrid materials 1 g to $NH_4F$ 50 mL and stirred at 70° C. The X-ray diffraction pattern showed that its crystallinity was maintained without being damaged after treating with ammonium fluoride. Further, the surface area of the porous organic-inorganic hybrid materials after treating with ammonium fluoride was measured to be 1,950 $m^2/g$.

Example 2

Porous organic-inorganic hybrid materials were prepared by the same method as Example 1, except that the mixture was prepared by further adding HF. The final molar ratio of the reaction material was $Fe(NO_3)_3 \cdot 6H_2O$:BTCA:$H_2O$:HF=1:0.66:11.3:0.15. The mixed reaction material was stirred in 500 rpm for 20 minutes at room temperature to make the reaction material uniform. While maintaining the Teflon reactor including said pre-treated reaction material at 120° C. for 12 hours, crystallization was performed. Then, the reaction material was cooled to room temperature, washed with distilled water and dried to obtain porous organic-inorganic hybrid materials (Fe-BTC). As a result of measuring the reaction pressure when preparing the porous organic-inorganic hybrid materials (Fe-BTC), the internal pressure at 120° C. was 1 bar. Without being bound by theory, it appears that such result comes from that Fe-BTC crystal rapidly adsorbs a solvent at 120° C.

It has been confirmed that the X-ray diffraction pattern was the same structure as that of Fe-BTC of a reference [Chemical Communication 2820, 2007]. As a result of ICP and EA analysis, it has been confirmed that the obtained porous organic-inorganic hybrid materials Fe-BTC were a material that can be represented by a formula $Fe_3O(H_2O)_2F_{0.85}(OH)_{0.15}[C_6H_3—(CO_2)_3]_2 \cdot nH_2O$ ($0 \leq y \leq 1$, $0 \leq n \leq 50$). After vacuum drying 0.1 g of the obtained porous organic-inorganic hybrid materials Fe-BTC at 70° C. for 30 minutes, a water adsorption test was performed by the gravimetric method. At room temperature on a relative humidity of 60%, the water adsorption amount per weight of the adsorbent was measured to be 0.8 g/g. As such, it can be shown that the porous organic-inorganic hybrid materials can easily adsorb and desorb water even at a low temperature of 100° C. or below, it can achieve a very excellent efficiency in humidifiers, dehumidifiers, etc.

Example 3

Porous organic-inorganic hybrid materials (Fe-BTC) were prepared in the same method as Example 1 except that iron chloride ($FeCl_3 \cdot 6H_2O$) was used as metal salt instead of iron nitrate. It has been confirmed that the X-ray diffraction pattern was the same structure as that of Fe-BTC of a reference [Chemical Communication 2820, 2007]. As a result of ICP and EA analysis, it has been confirmed that the obtained porous organic-inorganic hybrid materials Fe-BTC were a material that can be represented by a formula $Fe_3O(H_2O)_2Cl_{0.80}(OH)_{0.20}[C_6H_3—(CO_2)_3]_2 \cdot nH_2O$ ($0 \leq y \leq 1$, $0 \leq n \leq 50$) where fluorine was not included.

Example 4

After adding $Cr(NO_3)_3 \cdot 9H_2O$, and 1,4-benzenedicarboxylic acid (BDCA) to a Teflon reactor, distilled water was added so that the final molar ratio of the reaction material was Cr:BDCA:$H_2O$=1:1:12. After putting the Teflon reactor including said reaction material in a reflux oven and reacting it for 11 hours at 210° C., it was cooled to room temperature, centrifuged, washed with distilled water and dried to obtain chromium terephthalate (chromium benzenedicarboxylate; Cr-BDC) whose surface area is 3,800 $m^2/g$ as porous organic-inorganic hybrid materials. After vacuum drying 0.1 g of the obtained organic-inorganic hybrid materials Cr-BDC at 70° C. for 30 minutes, a water adsorption test was performed by the gravimetric method. At a relative humidity of 60%, the water adsorption amount per weight of the adsorbent was measured to be 1.2 g/g (within 3 hours).

Example 5

Porous organic-inorganic hybrid materials (Fe-BTC) were prepared in the same method as Example 1 except that the reaction temperature is 100° C. It has been confirmed that the X-ray diffraction pattern was the same structure as that of Fe-BTC of a reference [Chemical Communication 2820, 2007], but as a result of ICP and EA analysis, it has been confirmed that the obtained porous organic-inorganic hybrid materials Fe-BTC were a material that can be represented by a formula $Fe_3O(H_2O)_2OH[C_6H_3-(CO_2)_3]_2 \cdot nH_2O$ ($0 \leq n \leq 50$) where fluorine was not included.

Example 6

Porous organic-inorganic hybrid materials were prepared in the same method as Example 1 except that aluminum nitrate hydrate was used instead of iron nitrate. As a result of measuring the nitrogen-adsorption amount after removing residual BTCA ligand by heating the obtained Al-BTC at 300° C. under nitrogen atmosphere, the surface area was 1,930 m$^2$/g.

Example 7

After adding metal (iron) chloride (FeCl$_3$) 40.8 mmol and 1,3,5-benzenetricarboxylic acid (BTCA) 26.8 mmol to a Teflon reactor, distilled water was added. The final molar ratio of the reaction material was FeCl$_3$:BTCA:H$_2$O=1:0.66:34. The mixed reaction material was stirred in 500 rpm for 20 minutes at room temperature to make the reaction material uniform. While maintaining the Teflon reactor including said pre-treated reaction material at 160° C. for 8 hours, crystallization was performed. Then, the reaction material was cooled to room temperature, washed with distilled water and dried to obtain porous organic-inorganic hybrid materials (Fe-BTC).

It has been confirmed that the X-ray diffraction pattern is same as that of MIL-100 (Fe) of a reference [Chemical Communication 2820, 2007]. As a result of ICP and EA analysis, it has been confirmed that the structure of the obtained porous organic-inorganic hybrid materials Fe-BTC were the same as that of MIL-100 where fluorine was not included, and was a material that can be represented by a formula $Fe_3O(H_2O)_2Cl[C_6H_3-(CO_2)_3]_2$. As a result of a nitrogen adsorption-desorption experiment, it has been confirmed that it had a surface area of 1,500 m$^2$/g and an adsorption amount of 450 mL/g at P/P$_0$=0.5. As a result of the analysis of electron microscope, it can be shown that the particle size became very small to 200-500 nm and below.

Porous organic-inorganic hybrid materials with improved surface area was prepared by removing impurities within the pores of hybrid materials after adding the prepared porous organic-inorganic hybrid materials 1 g to NH$_4$F 50 mL and stirred at 70° C. The X-ray diffraction pattern showed that its crystallinity was maintained without being damaged after treating with ammonium fluoride. Further, the surface area of the porous organic-inorganic hybrid materials after treating with ammonium fluoride was measured to be 1,820 m$^2$/g and an adsorption amount of 550 mL/g at P/P$_0$=0.5.

Example 8

Porous organic-inorganic hybrid materials were prepared in the same manner as in Example 7 except that VCl$_3$ was used instead of FeCl$_3$ as in Example 7. The X-ray diffraction pattern showed that the material having the same structure as in Example 7 was obtained. The electron microscope photograph showed that the porous organic-inorganic hybrid materials having uniform particle size of about 100 nm were obtained.

Example 9

A pellet was prepared from Fe-BTC powder obtained in Example 1 by using an eccentric press (EKO type by Korsch company). First, in order to increase adhesiveness between particles to be molded, after mixing graphite 3% by weight with Fe-BTC 97% by weight, ball milling was performed for 24 hours. After mixing and ball milling, it has been confirmed that the crystallinity of powder was not almost changed compared to pure Fe-BTC. After molding the ball milling powder by using the eccentric press, a Fe-BTC pellet having 3 mm diameter where the crystallinity is reduced by about 20% was obtained.

Example 10

After adding water 10% by weight to Fe-BTC powder of Example 1 and introducing the kneaded Fe-BTC slurry to a cylinder-type extruder with the internal of the extruder maintained vacuum, an extruded article was prepared at a cylinder rotating rate 50 rpm and at a molding rate 300 mm/min. The prepared extruded article was dried at 80° C. for 12 hours, and then heated at 120° C. for 2 hours by using an oven. The BET surface area of the final extrusion-molded article was 1,710 m$^2$/g.

Example 11

After adding water 10% by weight to Fe-BTC powder of Example 1 including 3% of BTC as a binder and introducing the kneaded Fe-BTC slurry to a cylinder-type extruder with the internal of the extruder maintained vacuum, an extruded article was prepared at a cylinder rotating rate 50 rpm and at a molding rate 300 mm/min. The prepared extruded article was dried at 80° C. for 12 hours, and then heated at 120° C. for 2 hours by using a oven. The BET surface area of the final extrusion-molded article was 1,750 m$^2$/g.

Comparative Example 1

After adding iron nitrate (Fe(NO$_3$)$_3$.6H$_2$O) 67 mmol and 1,3,5-benzenetricarboxylic acid (BTCA) 44 mmol to a Teflon reactor, distilled water was added. The final molar ratio of the reaction material was Fe(NO$_3$)$_3$.6H$_2$O:BTCA:H$_2$O=1:0.66:278. The mixed reaction material was stirred in 500 rpm for 20 minutes at room temperature to make the reaction material uniform. While maintaining the Teflon reactor including said pre-treated reaction material at 160° C. for 12 hours, crystallization was performed. Then, the reaction material was cooled to room temperature, washed with distilled water and dried to obtain porous organic-inorganic hybrid materials (Fe-BTC). It has been confirmed that the X-ray diffraction pattern is same as that of Fe-BTC of a reference [Chemical Communication 2820, 2007]. As a result of ICP and EA analysis, it has been confirmed that the obtained porous organic-inorganic hybrid materials Fe-BTC were a material that can be represented by a formula $Fe_3O(H_2O)_2OH[C_6H_3—(CO_2)_3]_2 \cdot nH_2O$ ($0 \leqq n \leqq 50$) where fluorine was not included. As a result of a nitrogen adsorption-desorption experiment, the surface area was 1,700 $m^2/g$. The yield of the porous organic-inorganic hybrid materials was 8 g per 1 L of the reactor.

Comparative Example 2

Carbon (Ecopro Carbon, specific surface area=665 $m^2/g$, pore volume=0.39 mL/g) used as a commercial water adsorbent was prepared. As a result of performing the water adsorption test under the same condition as Example 2 after vacuum drying said carbon adsorbent at 100° C. for 30 minutes, the water adsorption amount was 0.36 g/g. That is, although the desorption temperature of the adsorbent of Example 2 was 70° C., the adsorbent of the present disclosure showed a water adsorption amount that is at least 2.2 times larger.

Comparative Example 3

Zeolite Y (Aldrich company, Si/Al=5.6, surface area=827 $m^2/g$, pore volume=0.35 ml/g) used as a commercial water adsorbent was prepared. As a result of performing the water adsorption test under the same condition as Example 2 after vacuum drying said zeolite Y adsorbent at 200° C. for 30 minutes, the water adsorption amount was 0.35 g/g. That is, although the desorption temperature of the adsorbent of Example 2 was 70° C., the adsorbent of the present disclosure showed a water adsorption amount that is at least 2.2 times larger.

From the results of the examples and comparative examples above, in comparison with prior processes synthesizing under high-pressure condition more than 3 atm, porous organic-inorganic hybrid materials having the same crystallinity were prepared by low-pressure process of 3 atm or less. In particular, it has been confirmed that the yield of organic-inorganic hybrid materials prepared according to the present disclosure increased by at least 2 times per unit volume of reactor, and also it has been confirmed that the surface area increased by at least 18% when treated with inorganic salt such as ammonium salt, potassium fluoride, etc. In particular, when used as a water adsorbent, the porous organic-inorganic hybrid materials easily desorb water at a low temperature of 100° C. or lower, and it can be shown that a very excellent efficiency as a humidifier, dehumidifier, etc. can be achieved using such properties. Further, it has been confirmed that specific harmful materials in gas phase or particulate phase including volatile organic compound, etc. could be effectively removed.

All publications, patent applications, issued patents, and other documents referred to in this specification are herein incorporated by reference as if each individual publication, patent application, issued patent, or other document was specifically and individually indicated to be incorporated by reference in its entirety. Definitions that are included in text incorporated by reference are excluded to the extent that they contradict definitions in this disclosure.

From the foregoing, it will be appreciated that various embodiments of the present disclosure have been described herein for purposes of illustration, and that various modifications may be made without departing from the scope and idea of the present disclosure. Accordingly, the various embodiments disclosed herein are not intended to be limiting, with the true scope and spirit being indicated by the following claims.

What is claimed is:

1. A method for preparing porous organic-inorganic hybrid materials with crystallinity comprising:
    preparing a reaction solution containing a mixture of at least one inorganic metal precursor, at least one organic compound which may act as a ligand, and a solvent (step 1); and
    forming porous organic-inorganic hybrid materials with crystallinity by reacting the reaction solution (step 2),
    wherein the reaction is conducted under the pressure of about 3 atm or less.

2. The method of claim 1, wherein a molar ratio of the solvent to the inorganic metal precursor in the reaction solution is about 100 or less.

3. The method of claim 1, wherein the metal precursor is at least one metal selected from the group consisting of Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Mg, Ca, Sr, Ba, Sc, Y, Al, Ga, In, Tl, Si, Ge, Sn, Pb, As, Sb and Bi, or at lease one compound comprising thereof.

4. The method of claim 1, wherein the metal precursor is at least one metal selected from the group consisting of Cr, Fe, Al, Cu, Mn, Ti, Zr, Sn and V, or at lease one compound comprising thereof.

5. The method of claim 1, wherein the organic compound which may act as a ligand in the step 1 is a compound containing at least one functional group selected from the group consisting of carboxyl group, anion group of carboxylic acid, amino group (—$NH_2$), imino grout

, amide group (—$CONH_2$), sulfonic acid group (—$SO_3H$), anion group of sulfonic acid (—$SO_3^-$), methanedithioic acid group (—$CS_2H$), anion group of methanedithioic acid (—$CS_2^-$), pyridine group and pyrazine group, or a mixture thereof.

6. The method of claim 5, wherein the compound containing anion group of carboxylic acid is derived from a compound selected from the group consisting of benzenedicarboxylic acid, naphthalenedicarboxylic acid, benzenetricarboxylic acid, naphthalenetricarboxylic acid, benzenetribenzoic acid, pyridinedicarboxylic acid, bipyridyldicarboxylic acid, formic acid, oxalic acid, malonic acid, succinic acid, glutaric acid, hexanedioic acid, heptanedioic acid and cyclohexyldicarboxylic acid.

7. The method of claim 1, wherein the method further comprising: purifying an impurity in the porous organic-inorganic hybrid materials obtained in the step 2 by treatment with an inorganic salt, an acid adjuster, a solvent, or a mixture thereof (step 3).

* * * * *